United States Patent
Simonsen

(10) Patent No.: US 11,937,865 B2
(45) Date of Patent: Mar. 26, 2024

(54) ELECTROSURGICAL PENCIL

(71) Applicant: SAFEAIR AG, Root Längenbold (CH)

(72) Inventor: Jesper Schantz Simonsen, Jyderup (DK)

(73) Assignee: Stryker European Operations Limited, Carrigtwohill (IE)

( * ) Notice: Subject to any disclaimer, the term of this patent is extended or adjusted under 35 U.S.C. 154(b) by 808 days.

(21) Appl. No.: 16/093,917

(22) PCT Filed: Apr. 4, 2017

(86) PCT No.: PCT/EP2017/057989
§ 371 (c)(1),
(2) Date: Oct. 15, 2018

(87) PCT Pub. No.: WO2017/178286
PCT Pub. Date: Oct. 19, 2017

(65) Prior Publication Data
US 2019/0110832 A1    Apr. 18, 2019

(30) Foreign Application Priority Data

Apr. 14, 2016  (EP) ...................... 16165395

(51) Int. Cl.
*A61B 18/14*  (2006.01)
*A61B 18/00*  (2006.01)

(52) U.S. Cl.
CPC ............. *A61B 18/1402* (2013.01); *A61B 2018/00589* (2013.01); *A61B 2018/00601* (2013.01); *A61B 2018/00607* (2013.01); *A61B 2217/005* (2013.01); *A61B 2218/007* (2013.01); *A61B 2218/008* (2013.01)

(58) Field of Classification Search
CPC ...... A61B 18/1402; A61B 2018/00589; A61B 2018/00601; A61B 2217/005; A61B 2218/007; A61B 2218/008
See application file for complete search history.

(56) References Cited

U.S. PATENT DOCUMENTS

| | | | |
|---|---|---|---|
| 6,458,125 B1 * | 10/2002 | Cosmescu | A61B 18/042 606/31 |
| 9,375,252 B2 * | 6/2016 | Coe | A61B 18/14 |
| 2006/0264928 A1 | 11/2006 | Kornerup | |

(Continued)

*Primary Examiner* — Linda C Dvorak
*Assistant Examiner* — Ryan T Clark
(74) *Attorney, Agent, or Firm* — McDonnell Boehnen Hulbert & Berghoff LLP

(57) ABSTRACT

An electro-surgical pencil comprising:
a housing forming an axially extending main suction passage from a proximal opening to a distal opening;
a tube forming an extension of the main suction passage from the proximal opening to a proximal extension opening, the tube being configured for telescoping movement through the proximal opening;
an electrode for cutting and/or coagulating tissue, the electrode being attached to the tube and extending axially from the proximal extension opening; and
a suction tip attached to the tube and forming a further extension of the suction passage.
Since both the tube and the suction tip are movable relative to the housing, a short and a long configuration can be obtained while good smoke removal capabilities are maintained.

20 Claims, 5 Drawing Sheets

(56) References Cited

U.S. PATENT DOCUMENTS

2014/0052131 A1* 2/2014 Busch-Madsen ............................ A61B 18/1477
606/41
2014/0257237 A1 9/2014 Cosmescu
2014/0257273 A1 9/2014 Cosmescu

* cited by examiner

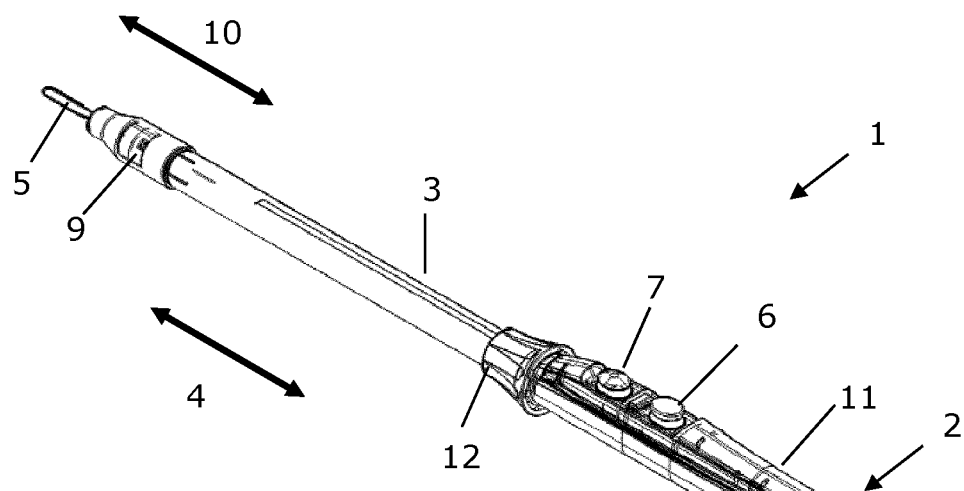
Fig. 1
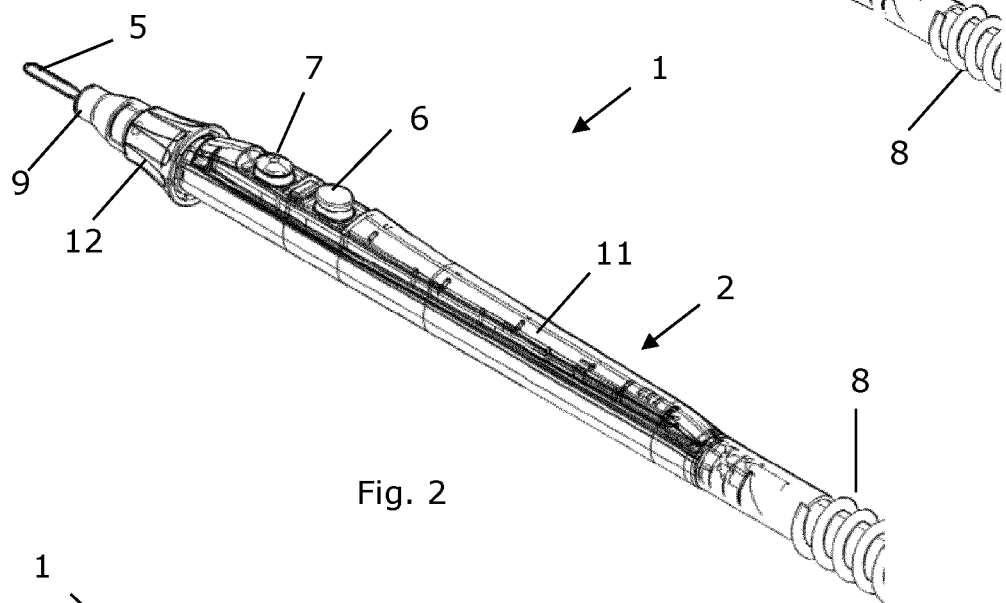
Fig. 2
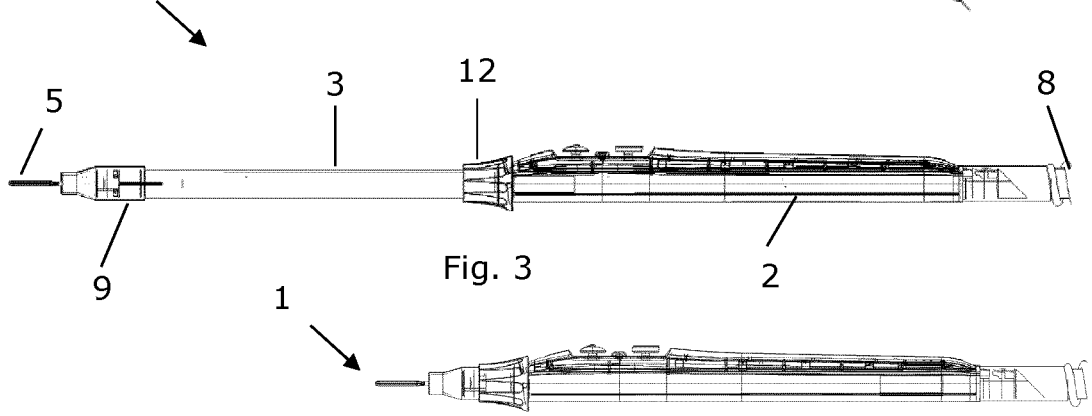
Fig. 3
Fig. 4

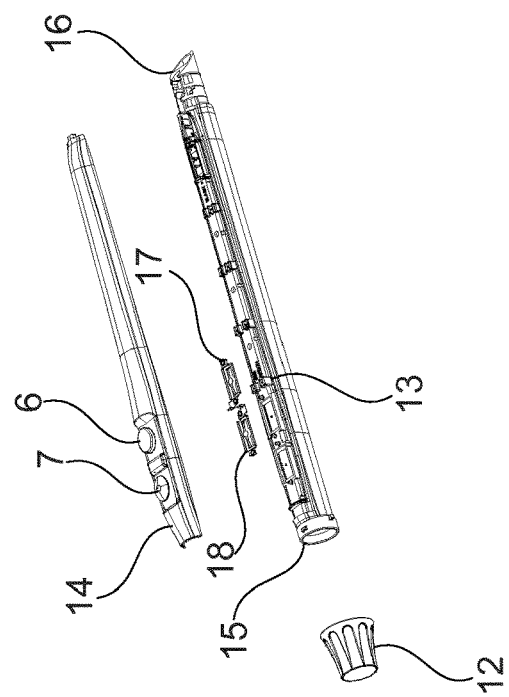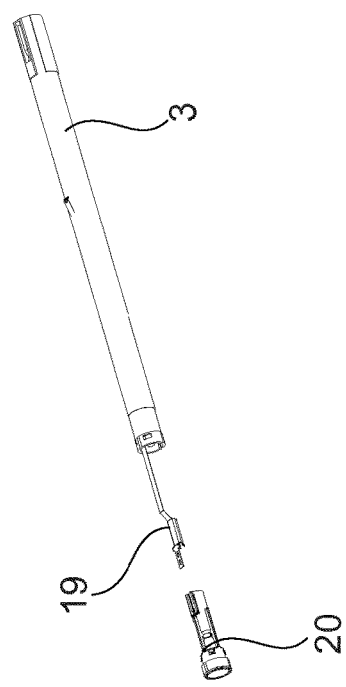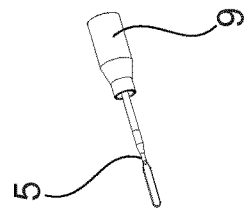
Fig. 5

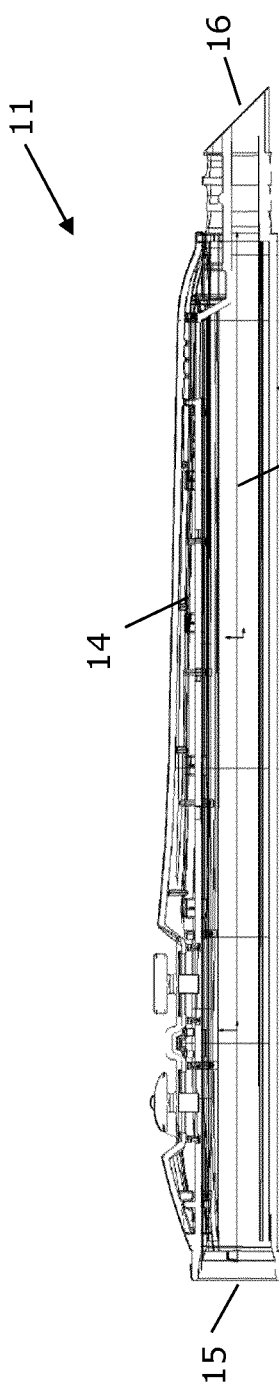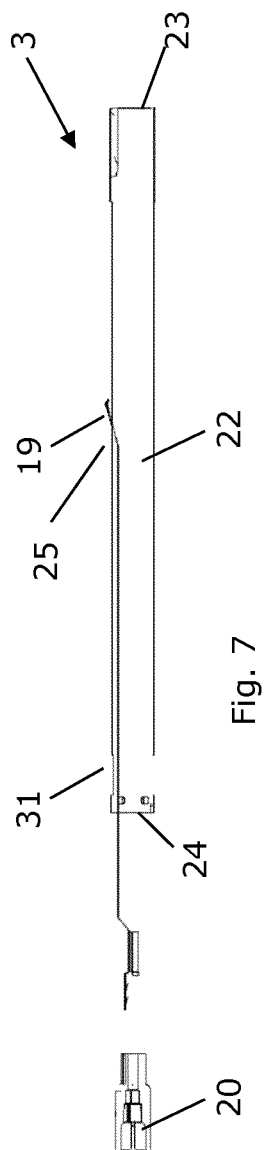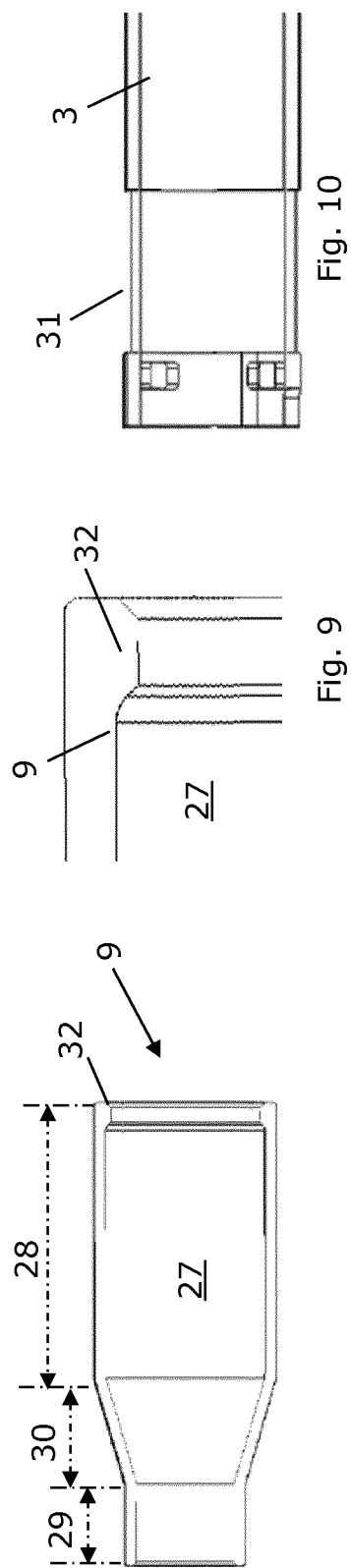

ELECTROSURGICAL PENCIL

INTRODUCTION

The present invention relates to an electrosurgical pencil for electrosurgical cutting or coagulation of tissue. The pencil comprises an elongated body, an exposed electrode, and telescoping means for changing a distance between the electrode and the elongated body.

BACKGROUND OF THE INVENTION

Electro-Surgical (ES) pencils are used in surgery, typically for cutting tissue and/or for coagulating blood. An ES pencil usually comprises a hand-piece into which electrodes of many different shapes and sizes may be placed. The electrode is supplied with a high frequency, typically Radio Frequency (RF), alternating current signal by an RF source. The RF source is typically called the Electro-Surgical Unit or ESU.

By varying the voltage and/or the frequency of the RF signal supplied by the ESU, the electrode can be used in different modes. Two common modes are a cutting mode and a coagulating mode.

During a surgical procedure it may be an advantage to provide a variable length of the pencil.

For that purpose, the electrodes come in different lengths, and by replacement of the electrode, the surgeon may configure the length of the pencil. An improved type of pencil includes a telescoping function by which the length of the pencil can be changed without necessitating replacement of the electrode.

Smoke generation during ES may reduce visibility and it may be unpleasant or even unhealthy for the surgeon and the surgical staff. Therefore smoke evacuation shrouds can be attached to an ES pencil for evacuating smoke close to the electrode.

SUMMARY OF THE INVENTION

To overcome problems with operating the existing pencils, and particularly to improve the ability to position the smoke evacuation shrouds close to the tip and yet obtain telescoping function of the pencil, the present invention, in a first aspect, provides an electro-surgical pencil comprising:
- a housing forming an axially extending main suction passage from a proximal opening to a distal opening;
- a tube with an internal conduit extending between a distal extension opening and a proximal extension opening and forming an extension of the main suction passage, the tube being configured for telescoping movement through the proximal opening;
- an electrode for cutting and/or coagulating tissue, the electrode being attached to the tube and extending axially from the proximal extension opening; and
- a suction tip attached to the tube and forming a further extension of the suction passage and being configured for telescoping movement relative to the tube to cover a larger or lesser portion of the electrode.

Since the tube is movable, the position of the electrode is adjustable relative to the housing and the surgeon can match the length of the pencil to a specific purpose. This is done by moving the tube into the housing to thereby create a short configuration, or by moving the tube out of the housing and thereby create a long configuration of the pencil.

Since also the suction tip is movable, the surgeon may adapt the position of the suction tip to a specific electrode and balance between the need for smoke evacuation and the need for unhindered view of the electrode tip where the cutting takes place. This is done by moving the suction tip away from the tube and housing to create a configuration where a larger portion of the electrode is covered and smoke evacuation takes place close to the tip of the electrode, or by moving the suction tip towards the tube and housing to create a configuration where a lesser portion of the electrode is covered thereby exposing the electrode for better visibility.

Since the suction tip specifically moves relative to the tube, the surgeon may set the position of the suction tip independently on the positioning of the tube relative to the housing. In that way, the surgeon may change the length of the pencil by adjusting the position of the tube and maintain the position of the suction tip relative to the electrode. This makes the use of the pencil efficient and prevents the need for repeated adjustment of the suction tip each time the length is adjusted.

Since the electrode extends axially from the proximal extension opening and the suction tip forms a further extension of the suction passage, it provides efficient smoke removal around the electrode. Particularly, the electrode may be fixed to a socket which is inside the extension of the main suction passage formed by the tube and thereby follow the movement of the tube relative to the housing.

The suction tip may be slidable along an inner surface inside the tube or along an outer surface outside the tube. By sliding the suction tip over the outer surface of the tube, the cross section of the suction tip may be larger, and the flow conditions in the suction passage can be improved. In an advantageous embodiment, the suction tip is slidable on an outer surface of the tube and receivable in a recess in the housing to thereby provide good suction properties and a particularly short pencil in the short configuration.

The term larger or smaller cross section herein refers to the area of a cross section perpendicular to the axial direction of the pencil. The axial direction is the direction from the proximal opening to the distal opening along the centre of the pencil. If the cross section has a circular shape, the diameter of that circular shape may express the size of the cross section.

When the tube is telescopically moved to the short configuration, the suction tip becomes located close to the housing. To prevent that the suction tip hinders access to hold and operate the pencil and to ensure a free outer surface of the housing, the suction tip may particularly be configured to be slidable partly into the housing. It may thus be configured to be slidable along an inner surface of the housing, e.g. an inner surface of the suction passage, or an inner surface of a recess formed in the housing at the proximal opening.

At the proximal opening, the housing may include a collar which enhances the grip by enlarging the radial dimension of the housing. In this embodiment, the housing comprises a main body forming the suction passage and the proximal opening, and a collar formed about the proximal opening. The collar may be operable, e.g. by rotation, for controlling movability of the tube relative to the housing, e.g. by reducing or increasing the friction against movement of the tube in the housing.

If the housing comprises a collar, the suction tip may be receivable into a space within the collar or between the collar and the main body of the housing whereby the collar forms the above mentioned inner surface of the housing against which the suction tip is slidable. The collar may provide two functions. It increases the cross section of the housing locally and thus improves the ergonomic characteristics of the pencil, and it facilitates locking and unlocking of the tube relative to the housing.

Since the suction tip is receivable in the recess between the collar and the main body, the tip of the suction tip can be positioned very close to the location where the user grips the pencil when gripping the collar. Accordingly, also the electrode tip may come very close to the position where the surgeon holds the pencil. The short distance between the gripping location and the electrode tip increases significantly the ability to correctly manoeuvre the electrode, and the combination between the collar and the recess which receives the suction tip therefore provides very good ergonomic properties of the pencil.

Since at least a portion of the suction tip is receivable into the mentioned space, the length of the pencil can be reduced not only by the telescopic movement of the tube into the housing but also by the movement of the suction tip into the housing, and a pencil with suction tip and movable from a relatively short configuration to a relatively long configuration can be obtained.

It is an object to increase the cross section of the suction passage. However, it is also an object to enable a small outer radial size of the suction tip since that may improve the ability to slide the suction tip into the housing without necessitating a large radial size of the housing. For this purpose, the tube may form a radially recessed portion and the suction tip may extend into the recessed portion. The recessed portion may particularly be formed between two sections of the tube which is not recessed such that the suction tip can be confined in the recessed portion. In that way, the recessed portion may limit axial movement of the suction tip relative to the tube. The recess may extend circumferentially and completely about the outer periphery of the tube, or the recess may form one or more discrete depressions in the outer surface of the tube.

The suction tip may comprise a widened distal section axially offset from a narrow proximal section, the widened distal section may have a larger cross section than the tube and the narrow proximal section may have a smaller cross section than the tube. In that way, the widened distal section may slide on an outer surface of the tube while the narrow proximal section may increase the flow speed of the smoke evacuation and provide better visibility to the tip of the electrode where the cutting takes place. Between the wide section and the narrow section, the suction tip may form a transition section providing gradually reduced cross section from the widened distal section to the narrow proximal section.

The widened distal section may have a cross section being at least twice the cross section of the narrow proximal section, e.g. three or four or five times the cross section of the narrow proximal section.

The tube and/or the suction tip may particularly have a circular cross section such that the suction tip can be rotated about the outer surface the tube.

The proximal opening may also have a circular cross section such that the tube can be rotated in the proximal opening.

The pencil may comprise a switching structure including a switch for controlling application of an electrosurgical RF signal to the electrode. During use, the surgeon will typically hold the pencil at a position where the switch can be operated while holding the housing in a firm grip. To provide a short distance and thus improved manoeuvrability of the switch, it may be an advantage to allow the tube and potentially a portion of the suction tip to slide below the switch such that the tube and the switch overlap each other in a direction perpendicular to the axial direction of the pencil. Alternatively, it may be arranged that the distance along the axial direction between the tube and the switch is smaller than the largest dimension of the housing in the cross section perpendicular to the axial direction.

The switching structure may particularly be isolated from the suction passage. In one embodiment, the switching structure is housed in a first compartment inside the housing and the suction passage is formed by a second and completely separate compartment inside the housing. This prevents ingress of tissue and fluid to impare the functioning of the switch.

The suction tip may comprise a threaded connection to the tube such that movement of the suction tip relative to the tube can be effected by rotation of the suction tip relative to the tube. Alternatively, the suction tip and tube comprises coorporating sliding surface forming a linear joint which enables linear sliding of the suction tip relative to the tube but prevents rotation of the suction tip relative to the tube.

In a second aspect, the invention provides a method of configuring an electro-surgical pencil which comprises:
  a housing forming an axially extending main suction passage from a proximal opening to a distal opening;
  a tube forming an extension of the main suction passage from the proximal opening to a proximal extension opening, the tube being configured for telescoping movement through the proximal opening;
  an electrode for cutting and/or coagulating tissue, the electrode being attached to the tube and extending axially from the proximal extension opening; and
  a suction tip forming a further extension of the suction passage and being configured for telescoping movement relative to the tube to cover a larger or lesser portion of the electrode, the method comprising the step of configuring the length of the pencil by moving the tube relative to the housing, and configuring the position of the suction tip relative to the electrode by moving the suction tip relative to the tube.

LIST OF DRAWINGS

The invention will be described in further details below with reference to the drawing, in which exemplary embodiments are shown in accordance with the present invention.

FIG. 1 illustrates a perspective view of a pencil according to the present invention in a long configuration;

FIG. 2 illustrates a perspective view of a pencil according to the present invention in a short configuration;

FIGS. 3-4 illustrate side views of the pencil in the long and short configuration;

FIG. 5 illustrates an exploded view of the pencil;

FIG. 6 illustrates a cross section of the housing;

FIG. 7 illustrates a cross section of the tube;

FIG. 8 illustrates a cross section of the suction tip;

FIG. 9 illustrates a detail of the suction tip;

FIG. 10 illustrates a detail of the tube;

DETAILED DESCRIPTION OF AN EMBODIMENT

Figure 11:
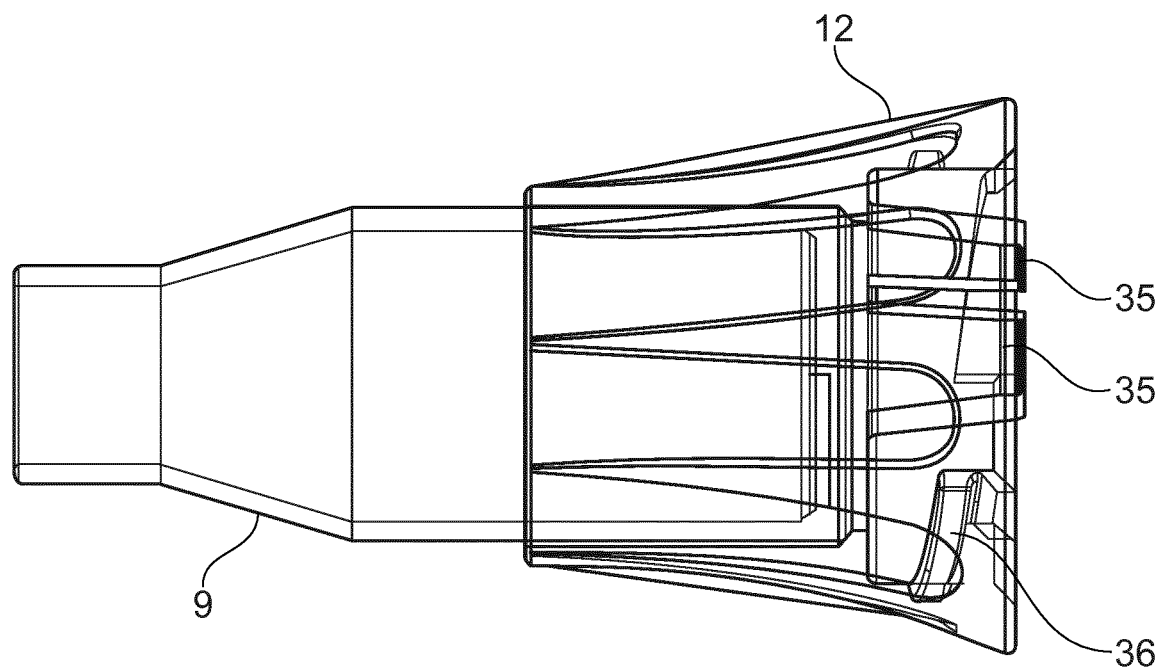
FIG. 11 illustrates a cross section of the collar and the suction tip.

It should be understood that the detailed description and specific examples, while indicating embodiments of the invention, are given by way of illustration only, since various changes and modifications within the spirit and scope of the invention will become apparent to those skilled in the art from the detailed description.

FIG. 1 illustrates an electro-surgical pencil 1 with a housing 2 The pencil includes a tube 3 being telescopically movable in a main suction passage such that the length of the pencil can be varied forwardly and rearwardly as illustrated by the arrow 4 to thereby define the long configuration illustrated in FIG. 1 and the short configuration illustrated in FIG. 2.

The pencil comprises an electrode 5 which is releasably attached to the proximal end of the tube. The electrode is connected to an RF generator and conducts an ES signal for cutting and/or coagulating tissue. The signal is controlled by the switches 6, 7, one switch providing a signal suitable for cutting and one switch providing a signal suitable for coagulation. The illustrated electrode and pencil are for monopolar cutting but it could also be for bipolar cutting.

The pencil defines an axially extending main suction passage shown in details in the later drawings. The suction passage extends from a proximal opening to a distal opening. At the distal opening, a suction tube 8 connects the pencil to a suction pump for establishing suction and thus smoke removal.

The pencil comprises a suction tip 9 attached to the proximal end of the tube and forming a further extension of the suction passage. The tip is movable forward and rearward relative to the tube as illustrated by the arrow 10 and being configured for telescoping movement relative to the tube. In that way, the suction passage can be extended relative to the electrode to cover a larger or lesser portion of the electrode and the surgeon can thereby adjust the pencil to balance between the configuration where very good suction is obtained by a suction tip close to the electrode tip and the configuration where very good visibility can be obtained by a suction tip at a distance from the electrode tip. When moving the tube relative to the housing, the tip may remain in a fixed position relative to the tube since it is attached to the tube and not to the housing.

The housing 2 comprises a main body 11 and a collar 12. The collar 12 is located at the proximal end of the housing and is rotational about the main body. The collar is configured to increase or decrease friction between an outer surface of the tube and the inner surface of the collar depending on the angular position of the collar relative to the main body and it thus functions to lock or unlock the tube in the suction passage.

FIG. 5 illustrates an exploded perspective view of the pencil. In this view, the main body 11 is split into a lower main body part 13 and an upper main body part 14. The lower main body part 13 forms an axially extending main suction passage from a proximal opening 15 to a distal opening 16. The suction tube 8 is connectable to the distal end. The upper main body part 14 houses electronic components completely separated from the suction passage, i.e. wiring and contacts. In FIG. 5, contact elements 17, 18 are located below the switches 6, 7 and connect the RF signal to the electrode 5. The RF signal is transferred to a first sliding connector formed inside the suction passage, and by sliding connection to a second sliding connector 19 on an outer surface of the tube 3. The RF signal is further transferred to the electrode connector 20.

FIG. 6 illustrates a cross section of the main body 11 including the main suction passage 21 extending between the proximal and distal openings 15, 16. The tube 8 is telescopically movable in the main suction passage and extends outwards from the proximal opening 15.

FIG. 7 illustrates a cross section of the tube 3 including the inner conduit 22 extending between a distal extension opening 23 and a proximal extension opening 24. By its inner conduit, the tube forms an extension of the main suction passage 21 from the proximal opening 15 to the proximal extension opening 24 in the proximal end of the tube. The second sliding connector 19 on the outer surface of the tube enters into the conduit 22 through an opening at the position 25 and extends towards the electrode connector 20.

FIG. 8 illustrates the suction tip 9 forming a further extension 27 of the suction passage. The suction tip is configured for telescoping movement relative to the tube 3 to cover a larger or lesser portion of the electrode.

The suction tip forms a widened distal section 28 which has a larger cross section than the tube and the inner surface of the widened section 28 can therefore slide on the outer surface of the tube. The suction tip further forms a narrow proximal section 29 with a smaller cross section than the tube. Between the widened and the narrow section, the suction tip forms a transition section 30 in which the cross section is gradually reduced from the widened distal section to the narrow proximal section. In the disclosed embodiment, the cross sections of the sections are circular, and the diameter is different. Particularly, the diameter of the narrow proximal section may be in the range of 65-95 percent of the diameter of the widened section.

FIG. 9 illustrates an enlarged view of the distal end of the suction tip and FIG. 10 illustrates an enlarged view of the proximal end of the tube 3. The tube forms a radially recessed portion 31 extending circumferentially and completely around the tube. The distal end of the suction tip is received in the recessed portion. More specifically, the distal portion of the suction tip forms a radial inward projection 32 which slides on the outer surface of the tube 3 in the recessed portion 31. The recessed portion thereby limits the movability of the suction tip relative to the tube.

FIG. 11 illustrates the proximal end of the pencil in the collapsed configuration. In this configuration, the suction tip 9 is partly received into the housing—more specifically into the space or recess below the collar 12 of the housing.

Figure 12:
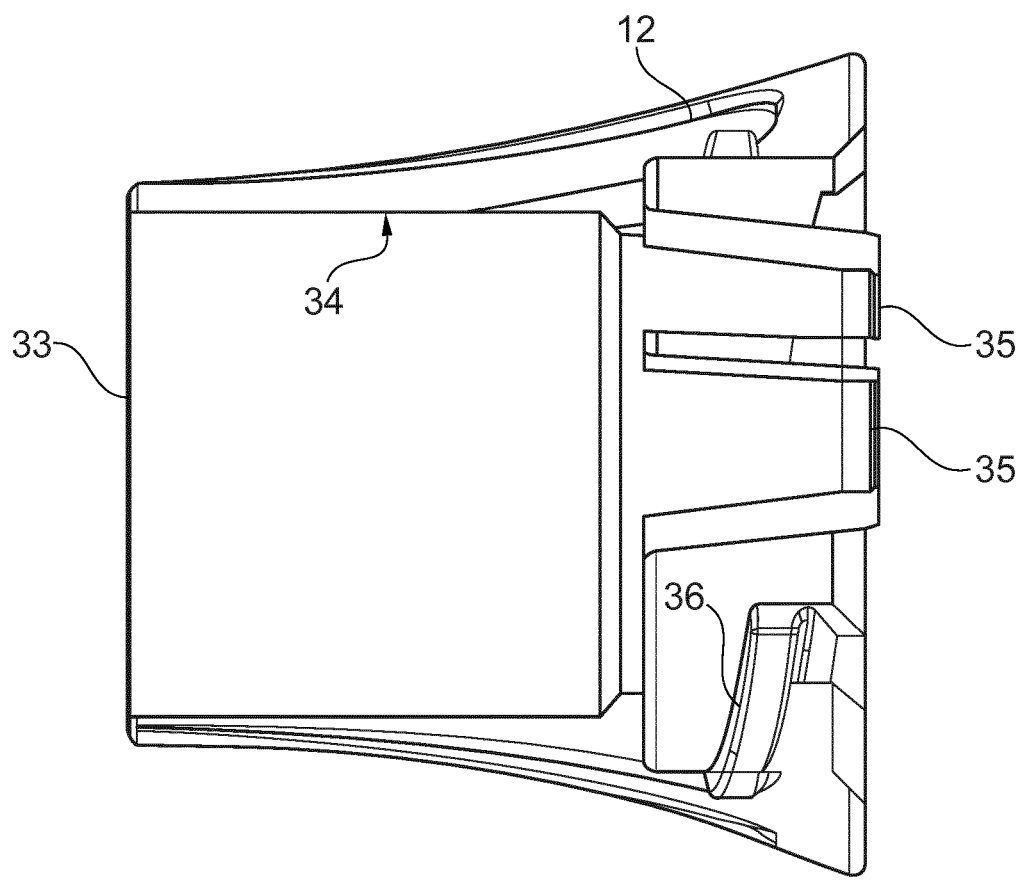
FIG. 12 illustrates a cross section of the collar.

FIG. 12 illustrates a cross section of the collar 12. The collar forms part of the housing and forms a proximal termination 33 thereof. Internally, the collar forms an inner sliding surface 34 on which the outer surface of the suction tip 9 slides when the suction tip is received in the recess of the collar.

Internally, the collar forms inner projections 35, and a thread portion 36. The inner projections 35 extend into the main suction passage and interact with a cam surface of the main body of the housing by rotation. In one position of the collar, the inner projections are released, and in another position of the collar, the projection is pressed radially inwardly by the cam of the housing. By the radial inwards deflection, the inner projections 35 are pressed against the tube 3 and therefore limits movement of the tube in the main suction passage. The collar thereby forms a fixing structure for fixing the position of the tube relative to the housing.

Figure 13:
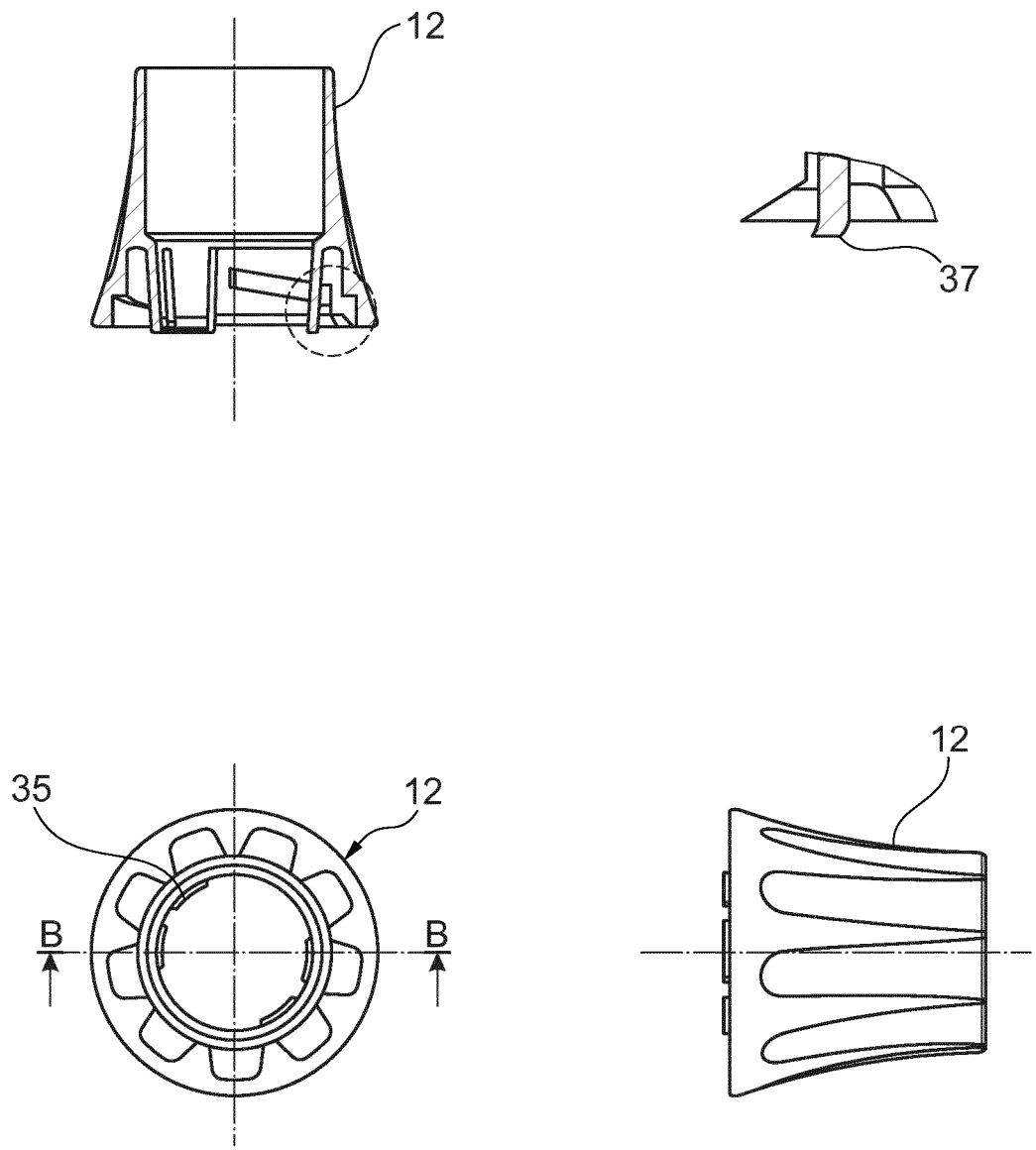
FIG. 13 illustrates further details of the collar.

FIG. 13 illustrates further details of the inner projections 35, and particularly illustrates that they extend into the suction passage and forms an edge capable of maintaining the position of the tube in the suction passage. FIG. 13 also illustrates that the projections 35 terminate in bended sections forming ridges or edges 37 which can be pressed into the outer surface of the tube.

The invention claimed is:

1. An electro-surgical pencil comprising:
a housing forming an axially extending main suction passage from a proximal opening to a distal opening, wherein the housing comprises (i) a main body forming the axially extending main suction passage and the distal opening, and (ii) a collar arranged about the proximal opening;
a tube with an internal conduit extending between a distal extension opening and a proximal extension opening and forming an extension of the axially extending main suction passage to the proximal extension opening, the tube being configured for telescoping movement through the proximal opening of the housing;
an electrode for cutting and/or coagulating tissue, the electrode being attached to the tube and extending axially from the proximal extension opening; and
a suction tip coupled to the tube and forming a further extension of the axially extending main suction passage,
wherein, while the electrode remains in a fixed position relative to the tube, the suction tip is configured for telescoping movement along an outer surface of the tube to adjust an extent by which the suction tip covers a portion of the electrode,
wherein the collar is rotatable about the main body to control movability of the tube relative to the housing,
wherein the collar is operable to adjust an amount of friction between an outer surface of the tube and an inner surface of the collar to lock and unlock the tube in the axially extending main suction passage, and
wherein the suction tip is slidable along the tube to a distal position at which at least a portion of the suction tip is received in a space between an inner surface of a proximal portion of the collar and the outer surface of the tube.

2. The electro-surgical pencil according to claim 1, wherein the collar forms a plurality of projections that are movable radially into the axially extending main suction passage of the housing upon rotation of the collar about the proximal opening.

3. The electro-surgical pencil according to claim 1, wherein the outer surface of the tube forms a radially recessed portion, and wherein the suction tip extends into the radially recessed portion.

4. The electro-surgical pencil according to claim 3, wherein the radially recessed portion limits axial movement of the suction tip relative to the tube.

5. The electro-surgical pencil of claim 4, wherein the radially recessed portion extends completely around a circumference the outer surface of the tube,
wherein a distal portion of the suction tip forms a radial inward projection which slides on the outer surface of the tube in the radially recessed portion.

6. The electro-surgical pencil according to claim 1, wherein the suction tip comprises a widened distal section axially offset from a narrow proximal section, the widened distal section having a larger cross section than the tube and the narrow proximal section having a smaller cross section than the tube.

7. The electro-surgical pencil according to claim 6, wherein the suction tip further comprises a transition section between the widened distal section and the narrow proximal section, the transition section providing gradually reduced cross section from the widened distal section to the narrow proximal section.

8. The electro-surgical pencil according to claim 6, wherein the widened distal section has a cross section being at least twice the cross section of the narrow proximal section.

9. The electro-surgical pencil according to claim 1, comprising at least one switch for controlling application of an electrosurgical radiofrequency (RF) signal to the electrode, wherein the tube is configured to slide in the axially extending main suction passage to a position at which the tube and the at least one switch overlap each other in a direction perpendicular to an axial direction of the electro-surgical pencil.

10. The electro-surgical pencil according to claim 1, wherein the tube forms a socket for releasably receiving the electrode, the socket being arranged in the further extension of the axially extending main suction passage and being in electrical communication with a switch located outside the axially extending main suction passage.

11. The electro-surgical pencil according to claim 1, wherein the suction tip comprises a threaded connection to the tube to cause axial movement of the suction tip relative to the tube by rotation of the suction tip relative to the tube.

12. The electro-surgical pencil of claim 1, wherein the space between an inner surface of a proximal portion of the collar and the outer surface of the tube extends between (i) a proximal end of the collar and (ii) a plurality of inner projections at a distal portion of the collar, and
wherein the plurality of inner projections press against the outer surface of the tube
wherein the proximal portion of the collar extends proximally of a proximal end of the main body of the housing,
wherein the suction tip is slidable along the outer surface of the tube to the distal position,
wherein when the suction tip is in the distal position, a distal end of the suction tip is proximal of the proximal end of the main body of the housing.

13. A method of operating an electro-surgical pencil, comprising:
providing an electro-surgical pencil comprising:
a housing forming an axially extending main suction passage from a proximal opening to a distal opening, wherein the housing comprises: (i) a main body forming the axially extending main suction passage and the distal opening and (ii) a collar arranged about the proximal opening;
a tube forming an extension of the main suction passage from the proximal opening to a proximal extension opening, the tube being configured for telescoping movement through the proximal opening;
an electrode for cutting and/or coagulating tissue, the electrode being attached to the tube and extending axially from the proximal extension opening; and
a suction tip coupled to the tube and forming a further extension of the axially extending main suction passage,
wherein, while the electrode remains in a fixed position relative to the tube, the suction tip is configured for telescoping movement along an outer surface of the tube to adjust an extent by which the suction tip covers a portion of the electrode,
wherein the collar is rotatable about the main body to control movability of the tube relative to the housing,
wherein the collar is operable to adjust an amount of friction between an outer surface of the tube and an inner surface of the collar to lock and unlock the tube in the main suction passage, and wherein the suction tip is slidable along the outer surface of the tube to a distal position at which at least a portion of the suction tip is received in a space between an inner surface of a proximal portion of the collar and the outer surface of the tube;

configuring a length of the electro-surgical pencil by moving the tube relative to the housing; and moving the suction tip relative to the tube to the distal position while the electrode remains fixed relative to the tube and the collar locks a position of the tube relative to the main suction passage.

14. The method of claim 13, further comprising rotating the collar about the proximal opening of the housing to control the movability of the tube relative to the housing.

15. The method of claim 14, wherein the collar forms a plurality of projections that are movable radially into the axially extending main suction passage of the housing upon rotation of the collar about the proximal opening.

16. The method of claim 13, wherein the outer surface of the tube forms a radially recessed portion, and wherein the suction tip extends into the radially recessed portion, wherein the method further comprises limiting, by the radially recessed portion, axial movement of the suction tip relative to the tube.

17. The method of claim 13, wherein the suction tip comprises a widened distal section axially offset from a narrow proximal section, the widened distal section having a larger cross section than the tube and the narrow proximal section having a smaller cross section than the tube, wherein the suction tip further comprises a transition section between the widened distal section and the narrow proximal section, the transition section providing gradually reduced cross section from the widened distal section to the narrow proximal section.

18. The method claim 13, comprising at least one switch for controlling application of an electrosurgical radiofrequency (RF) signal to the electrode, wherein configuring the length of the electro-surgical pencil by moving the tube relative to the housing comprises sliding the tube in the axially extending main suction passage to a position at which the tube and the at least one switch overlap each other in a direction perpendicular to an axial direction of the electrosurgical pencil.

19. The method of claim 13, further comprising releasably receiving the electrode in a socket formed by the tube, the socket being arranged in the further extension of the main suction passage and being in electrical communication with a switch located outside the axially extending main suction passage.

20. The method of claim 13, wherein the space between an inner surface of a proximal portion of the collar and the outer surface of the tube extends between (i) a proximal end of the collar and (ii) a plurality of inner projections at a distal portion of the collar, and wherein the plurality of inner projections press against the outer surface of the tube.

* * * * *